United States Patent
Hattori et al.

[11] Patent Number: 5,843,408
[45] Date of Patent: Dec. 1, 1998

[54] SEMI-PASTE ORAL PREPARATIONS

[75] Inventors: Masayuki Hattori; Akiko Fukushima, both of Kanagawa, Japan

[73] Assignee: Euro-Celtique, S.A., Luxembourg, Luxembourg

[21] Appl. No.: 761,145

[22] Filed: Dec. 6, 1996

Related U.S. Application Data

[63] Continuation of Ser. No. 360,470, Dec. 21, 1994, abandoned.

[30] Foreign Application Priority Data

Dec. 22, 1993 [JP] Japan ..................................... 5-323653

[51] Int. Cl.$^6$ ....................................................... A61K 7/16
[52] U.S. Cl. ................................................ 424/49; 424/51
[58] Field of Search ......................................... 424/49, 51

[56] References Cited

U.S. PATENT DOCUMENTS

| | | | |
|---|---|---|---|
| 4,567,036 | 1/1986 | Simon et al. | 424/51 |
| 5,057,497 | 10/1991 | Calam et al. | 514/21 |
| 5,126,127 | 6/1992 | Bhagwat et al. | 424/78.25 |

*Primary Examiner*—Shelley A. Dodson
*Assistant Examiner*—Michael A. Williamson
*Attorney, Agent, or Firm*—Davidson, Davidson & Kappel, LLC

[57] ABSTRACT

A semi-paste oral preparation comprises, as effective ingredients, at least 0.1 to 20% by weight of povidone-iodine based on the total weight of the preparation, and 0 to 50 parts by weight of potassium iodide and 1 to 300 parts by weight of a sugar alcohol of an oligosaccharide as a base and stabilizer, the parts by weight being based on one part by weight of the povidone-iodine. This semi-paste oral preparation has a modest viscosity, good taste and good stability upon storage for a long time.

12 Claims, No Drawings

SEMI-PASTE ORAL PREPARATIONS

This application is a continuation, of application Ser. No. 08/360,470 filed Dec. 21, 1994, now abandoned.

BACKGROUND OF THE INVENTION

The present invention relates to a semi-paste oral preparation (toothpaste) comprising povidone-iodine.

In U.S. Pat. No. 5,126,127 (Bhagwat, et al.) the microbicidal, bactericidal, germicidal and antiseptic properties of povidone-iodine were demonstrated with respect to stable ophthalmic povidone-iodine solutions. The ophthalmic solutions disclosed therein comprise a microbicidally effective amount of available iodine ions (about 0.03% to about 0.06%) and a suitable alkalinizing agent for prolonged stability of the preparation.

It is well known that povidone-iodine is effective against pathogenic bacteria for periodontal diseases: "SHIKAI TENBO (Dental Review)" Vol. 70, No. 6 (1987) p. 1409–1415; "Proceedings of 1989 Meeting of the Dental Society in Nippon Dental University", p. 26, Sep. 10, 1989. It is also known that potassium and/or sodium iodide is used as a stabilizer for solutions containing povidone-iodine, and that potassium and/or sodium iodide and sodium and/or potassium chloride are used as stabilizers for dentifrices: Japanese Patent Application Laying Open (Kokai) Nos. 2-213348 and 4-173726 and Japanese Patent Application No. 4-156341. In order to ensure the quality of these preparations during distribution thereof in the market, however, it is necessary to formulate large amounts of the stabilizers into these preparations, resulting in a salty taste or rendering the preparation irritating. Accordingly, stabilizers of better taste would be desirable in view of feeling and/or mouth-feel upon use.

Maltitol (reducing maltose) and lactitol (reducing lactose), which are sugar alcohols of oligosaccharides, have been used as wet humectants for dentifrices since they are more viscous and have a higher specific gravity, more excellent humectant property and better flavor and taste as compared with conventional ones. Japanese Patent Publication (Kokoku) No. 40-15120 and Japanese Patent Application Laying Open (Kokai) No. 49-31832. However, maltitol and lactitol have never been used as stabilizers for povidone-iodine or bases of semi-paste preparations for treating or preventing gingivitis, pyorrhea alveolaris and stomatitis, although they are used as wet humectants for dentifrices due to their excellent humectant properties.

OBJECTS AND SUMMARY OF THE INVENTION

It is an object of the present invention to provide a semi-paste oral preparation for treating and preventing gingivitis, pyorrhea alveolaris, stomatitis, plaque, dental caries, halitosis and other conditions caused by microbes that are susceptible to the microbicidal or antiseptic properties of povidone-iodine or iodine. The preparation, which contains povidone-iodine, has a modest viscosity, good taste and good stability upon storage for a long period of time.

The present invention provides a semi-paste oral preparation comprising, as effective ingredients, at least 0.1 to 20% by weight of povidone-iodine based on the total weight of the preparation, and 0 to 50 parts by weight of potassium iodide and 1 to 300 parts by weight of a sugar alcohol of an oligosaccharide as a base and stabilizer, the parts by weight being based on one part by weight of the povidone-iodine.

The present invention also relates to the treatment and/or prevention of oral conditions or disease states of the mouth which may be treated with povidone iodine. A povidone-iodine preparation according to the present invention will be applied to peri-oral surfaces or tissues, or oral cavity or tissues and structures therein by any means known in the art. The amount of preparation that will be applied may vary in quantity or strength, but will be sufficient to supply a suitable amount of povidone-iodine preparation such that an effective amount of iodine is delivered to the desired site to produce a microbicidal or antiseptic effect.

In preferred embodiments, delivery of the semi-paste povidone-iodine preparation may be accomplished, for example, by applying a desired amount of the preparation to a tooth-brush and manipulating the toothbrush such that the preparation is applied to the intended tissues or structures in the oral cavity or peri-oral area.

In a preferred embodiment the method of prevention or treatment of oral diseases or conditions includes the steps of applying to a desired site within the oral cavity or peri-oral area of a patient in need of prevention or treatment of an oral disease or condition a microbicidally effective amount of a semi-paste oral preparation. The semi-paste oral preparation comprises at least from about 0.1 to about 20% by weight of povidone-iodine based on the total weight of the preparation, from about 0 to about 50 parts by weight of potassium iodide and from about 1 to about 300 parts by weight of a sugar alcohol of an oligosaccharide as a base and stabilizer, the parts by weight being based on one part by weight of the povidone-iodine.

The method of prevention or treatment of oral diseases or conditions are useful in treating or preventing oral diseases or conditions such as gingivitis, pyorrhea alveolaris, stomatitis, dental plaque, dental caries, halitosis and other oral disease states which are caused substantially or which result substantially from microbes which succumb to the microbicidal or antiseptic properties of povidone-iodine or iodine.

DETAILED DESCRIPTION

One aspect of the present invention relates to the treatment and/or prevention of oral conditions or disease states of the mouth which may be treated with povidone iodine. A povidone-iodine preparation according to the present invention will be applied to per-oral surfaces or tissues, oral cavity or tissues and structures therein by any means known in the art. The amount of preparation that will be applied may vary in quantity or strength, but will be sufficient to supply a suitable amount of povidone-iodine preparation such that an effective amount of iodine is delivered to the desired situs to produce a microbicidal or antiseptic effect.

In preferred embodiments, delivery of the semi-paste povidone-iodine preparation may be accomplished, for example, by applying a desired amount of preparation to a tooth-brush and manipulating the toothbrush such that the preparation is applied to the intended tissues or structures in the oral cavity.

The semi-paste preparations of the present invention are useful for treating or preventing gingivitis, pyorrhea alveolaris and stomatitis.

Other oral conditions and diseases are caused by or result from microbes or microbial processes. Dental plaque is thought to be caused by bacteria that produce, along with acids, long-chain polymers such as dextrans and levans that adhere to a pellicle or tooth surface, forming a sticky adherent mass which accumulates over time. Food residues may adhere to the mass which are then degraded by bacteria into more dextrans, levans and acids. The accumulation of acids and other products on the tooth surface are known to cause dental caries.

Halitosis is often the result of the microbial degradation of food products, oral infections, caries or other microbial related conditions or disease states. Other periodontal infections or conditions caused by microbes may cause halitosis.

It is contemplated that conditions such as plaque, halitosis, dental caries and the like may be either treated and/or prevented by the povidone-iodine preparations of the present invention. This effect is a natural result of the expectation that because povidone-iodine possesses microbicidal, antibacterial and antiseptic properties, application of these preparations in a pharmaceutically sufficient amount will remove or reduce the microbes that underly these conditions or disease states.

The semi-paste oral preparation according to the present invention has a pH in the range from 1.5 to 7.5, preferably from 3.0 to 5.0. The physico-chemical properties required for a base of semi-paste oral preparations for treating and preventing gingivitis, pyorrhea alveolaris or stomatitis are an appropriate viscosity, good taste and chemical stability. The present inventors have chosen sugar alcohols, which have been chemically stabilized by reducing saccharides, as the base satisfying the requirements.

The saccharides include monosaccharides, oligosaccharides and polysaccharides. So far as the viscosity is concerned, it is possible to use a sugar alcohol of a monosaccharide, such as sorbitol, xylitol and mannitol, as a base in combination with a thickener so as to produce a preparation having a suitable viscosity. However, such a thickener may affect the stability of povidone-iodine and is unsuitable for attaining the object of the present invention.

Sugar alcohols of oligosaccharides, such as maltitol, lactitol, maltitritol and maltitetraol, are suitable herein since an appropriate viscosity is provided. A sugar alcohol of a polysaccharide may provide a higher viscosity as compared with the oligosaccharides; however, some combinations of a polysaccharide and an oligosaccharide may provide a suitable viscosity.

Povidone-iodine is chemically very active and unstable. When it is formulated with a conventionally used thickener and allowed to stand at ordinary temperature, the effective iodine content thereof significantly reduces in several days. In order to improve the stability of a preparation containing povidone-iodine, 2 to 3% by weight of potassium and/or sodium iodide and 5 to 10% by weight of sodium and/or potassium chloride have been formulated thereinto. However, these formulations have an irritant and/or salty taste resulting in unfavorable feeling upon use, although the stability is improved.

Saccharides will react with povidone-iodine and the effective iodine content reduces with the lapse of time: therefore, desired preparations cannot be obtained. On the contrary, sugar alcohols produced by substantially fully reducing saccharides, in general, are relatively unreactive with povidone-iodine and accordingly the povidone-iodine mixed with the sugar alcohols is stable for a long time. The stability of povidone-iodine upon storage is related to the degree of reduction of a saccharide used. Thus, it is important to use a sugar alcohol reduced as completely as possible in order to obtain a preparation having better stability. Unreduced materials contained in such a preparation must be maintained at 5% by weight of the preparation or below.

Among sugar alcohols of oligosaccharides, substantially fully reduced products of a syrup containing about 75% maltose (w/w), which are compositions based on maltitol, that is so-called reducing maltose syrup, may be used to provide excellent stability and semi-paste-like quality, as well as other properties. In this case, unreduced products, that is saccharides, which are impurities in the reducing maltose syrup will affect the stability of povidone-iodine. Thus, the degree of reduction of maltose in the reducing maltose syrup used should be at least about 95%, preferably about 98% or higher.

In the reducing maltose syrup, other sugar alcohols of oligosaccharides than maltitol, such as maltitritol and maltitetraol, may also be effective in improving the stability of povidone-iodine. The viscosity of the preparation increases with the content of saccharides having a higher molecular weight. A suitable viscosity can be obtained by adjusting the ratio of saccharides with a smaller molecular weight to those with a higher molecular weight.

In addition to the above described effective ingredients and base, the semi-paste oral preparation of the present invention may optionally contain a wetting agent, thickener, foaming agent, stabilizer, sweetening agent, antiseptic, perfume, coloring agent, etc.

Illustrative examples of such optional additives are mentioned below:

Wetting agents may include glycerin, sorbitol, propylene glycol and polyethylene glycol. Examples of thickeners include sodium carboxymethyl cellulose, hydroxyethyl cellulose, carrageenan, sodium alginate, xanthane gum, polysodium acrylate, polyvinyl alcohol, Locust bean gum, carbopol, guar gum, montmorillonite, gelatin, carboxyvinyl polymer, hydroxypropyl methyl cellulose, and the like.

Foaming agents may include sodium laurylsulfate, sodium α-olefinsulfates, N-acylgarcosinates, N-acylglutamates, N-acyltaurates, sucrose fatty acid estes, Armalolamide, polyoxyethylene hydrogenated castor oil, and polyglycerin fatty acid esters and the like.

Illustrative examples of sweetening agents include saccharin sodium, itevioside, p-methoxycinnamin aldehyde, neohesperidyl dihydrochalaoone, perillartine and the like.

Examples of antiseptics may include p-oxyhydroxy-benzoic esters, sodium benzoate and the like.

Other effective additives may include fluorides such as sodium, potassium, ammonium and stannous fluoride and sodium monofluorophogphate; allantoin chlorohydroxy ammonium, hinokitiol, tranoxamae acid, ascorbic acid, lysozyme chloride, glycyrrhizic acid and its salts, sodium chloride, dl-α-tocopherol acetate, α-bigabolol, isopropylmethylphenol, chlorhexidine salts, cetylpyridinium chloride, azulone, glycyrrhetic acid, sodium copper chlorophyllin, aluminium lactate, berberine, hydroxamic acid and its derivatives, dextranase, mutanase amylase, epicihydrochlolesterol, benzethonium chloride, dihydrocholesterol, zinc citrate, Japanese angelica root soft extracts, and extracts of clove, rosemary, scutellaria root and safflower or other suitable agents known in the pharmaceutical art.

Perfumes may include 1-menthol and anethole and coloring agents may include Blue No. 1 and Yellow No. 5 (F.D. & C.) or other suitable perfume or coloring agents known in the pharmaceutical art.

DETAILED DESCRIPTIONS OF THE PREFERRED EMBODIMENTS

The following examples illustrate various aspects of the present invention. They are not to be construed to limit the claims in any manner whatsoever.

EXAMPLES

Comparative Examples 1 and 2:

|  | Comp. Ex.1 | Comp. Ex. 2 |
|---|---|---|
| Povidone-iodine | 5.00 g | 5.00 g |
| Potassium iodide | 1.00 g | 1.00 g |
| Sorbitol | 45.00 g | 45.00 g |
| Sodium carboxymethyl cellulose | — | 2.00 g |
| Sodium lauryl sulphate | 1.00 g | 1.00 g |
| Saccharin sodium | 0.10 g | 0.10 g |
| L-Menthol | 0.40 g | 0.40 g |
| Ethanol | 0.50 g | 0.50 g |
| Concentrated glycerin | q.s. | q.s. |
| Total | 100.00 g | 100.00 g |
| Remaining effective iodine (%) | | |
| Storage at 60° C. | | |
| for 1 week | 89% | 61% |
| for 2 weeks | 84% | 52% |
| Storage at 40° C. | | |
| for 1 month | 94% | 86 |
| for 2 months | 91% | 75 |
| for 3 months | 90% | 67 |

These formulations (Comparative Examples 1 and 2) were prepared using a syrup of sorbitol containing about 70% of the monosaccharide which approximated to the upper solubility limit and examined for feeling and/or mouth-feel upon use. The formulation of Comparative Example 1 was too low in formulation of Comparative Example 2 to which a thickener sodium carboxymethyl cellulose was added had a viscosity suitable for semi-paste oral preparation. Said formulations were each put into a polyethylene container and stored under the condition of 60° or 40° C. The amount of effective iodine was measured to evaluate its remaining percentage. The formulation of Comparative Example 1 was stable. In the formulation of Comparative Example 2, however, the povidone-iodine was unstable and this formulation was difficult to be made into an end preparation.

Comparative Examples 3 and 4

|  | Comp.Ex. 3 | Comp.Ex. 4 |
|---|---|---|
| Povidone-iodine | 5.00 g | 5.00 g |
| Potassium iodide | 1.00 g | 1.00 g |
| Xylitol | 41.00 g | 41.00 g |
| Poly(sodium acrylate) | — | 2.00 g |
| Sodium lauryl sulphate | 1.00 g | 1.00 g |
| Saccharin sodium | 0.10 g | 0.10 g |
| L-Menthol | 0.45 g | 0.45 g |
| Ethanol | 0.50 g | 0.50 g |
| Concentrated glycerin | q.s. | q.s. |
| Total | 100.00 g | 100.00 g |
| Remaining effective iodine (%) | | |
| Storage at 60° C. | | |
| for 1 week | 92% | 32% |
| for 2 weeks | 85% | 23% |
| Storage at 40° C. | | |
| for 1 month | 94% | 74% |
| for 2 months | 92% | 56% |
| for 3 months | 91% | 48% |

A xylitol solution containing 64% (w/w) of the monosaccharide which approximated to the upper solubility limit was preliminarily prepared and then the formulations (Comparative Examples 3 and 4) were prepared and examined for feeling and/or mouth-feel upon use. The formulation of Comparative Example 3 was too low in viscosity and unsuitable for semi-paste oral preparation, like that of Comparative Example 1. The formulation of Comparative Example 4 to which a thickener poly(sodium acrylate) was added had a viscosity suitable for semi-paste oral preparation. Said formulations were each put into a polyethylene container and stored under the condition of about 60° or about 40° C. The amount of effective iodine was measured to evaluate its remaining percentage. The formulation of Comparative Example 3 was stable. In the formulation of Comparative Example 4, however, the povidone-iodine was unstable and this formulation was difficult to be made into an end preparation.

Examples 1 and 2 and Comparative Example 5

|  | Comp Ex.5 | Ex.1 | Ex.2 |
|---|---|---|---|
| Povidone-iodine | 5.00 g | 5.00 g | 5.00 g |
| Potassium iodide | 1.00 g | 1.00 g | 1.00 g |
| 75% Maltose syrup | 64.00 g | — | — |
| 75% Reducing Maltose Syrup | — | 64.00 g | — |
| Reducing lactose | — | — | 36.00 g |
| Sodium carboxymethyl cellulose | 1.00 g | 1.00 g | 1.00 g |
| Sodium lauryl sulphate | 1.00 g | 1.00 g | 1.00 g |
| B-menthol | 0.45 g | 0.45 g | 0.45 g |
| Ethanol | 0.50 g | 0.50 g | 0.50 g |
| Concentrated glycerin | q.s. | q.s. | q.s. |
| Total | 100.00 g | 100.00 g | 100.00 g |
| Remaining effective iodine (%) | | | |
| Storage at 60° C. | | | |
| for 1 week | 47% | 90% | 93% |
| for 2 weeks | 39% | 81% | 82% |
| Storage at 40° C. | | | |
| for 1 month | 49% | 91% | 91% |
| for 2 months | 44% | 90% | 91% |
| for 3 months | 41% | 86% | 87% |

Two disaccharides maltose and lactose as well as their sugar alcohols, reducing maltose and reducing maltose, were examined for their solubility and it was found that their concentrations were 31%, 14%, 63% and 57% (w/w), respectively. Lactose was low in solubility and unsuitable for base of semi-paste oral preparation. The formulations (Comparative Example 5 and Examples 1 and 2) were prepared using maltose, reducing maltose and reducing lactose. These formulations were each put into a polyethylene container and stored under condition of about 60° or 40° C. The amount of effective iodine was measured to evaluate its remaining percentage. The formulations of Examples 1 and 2 were stable and could be made into an end preparation. However, the formulation of Comparative Example 5 was less stable than those of Examples 1 and 2 and difficult to be made into an end preparation.

The semi-paste oral preparation according to the present invention has a good stability on storage for a long time, good taste, a suitable viscosity and excellent feeling and/or mouth-feel upon use.

The examples provided above are not meant to be exclusive. Many other variations of the present invention would be obvious to those skilled in the art, and are contemplated to be within the scope of the appended claims.

What is claimed is:

1. A pharmaceutically stable povidone-iodine semi-paste oral preparation comprising at least from about 0.1 to about 20% by weight of povidone-iodine based on the total weight of the preparation, about 0 to about 50 parts by weight of potassium iodide and from about 1 to about 300 parts by weight of a pharmaceutically stable base comprising a substantially fully reduced oligosaccharide; wherein said base is substantially less reactive with said povidone-iodine relative to the reactivity of non-reduced oligosaccharide with PVI, and said preparation is homogeneous and pharmaceutically stable relative to an equivalent formulation comprising a non-reduced oligosaccharide.

2. A method of prevention or treatment of oral or peri-oral diseases or conditions comprising the steps of applying to a desired site within the oral cavity or peri-oral area of a patient in need of prevention or treatment of an oral disease or condition a microbicidal or antiseptically effective amount of the semi-paste oral preparation of claim 1.

3. The method of prevention or treatment of oral diseases or conditions of claim 2, wherein said oral diseases or conditions are selected from the group consisting of gingivitis, pyorrhea alveolaris, stomatitis, dental plaque, dental caries, halitosis and other oral disease states which are caused substantially or which result substantially from microbes which succumb to the microbicidal or antiseptic properties of povidone-iodine or iodine.

4. The semi-paste oral preparation of claim 1, wherein said base comprises a substantially reduced oligosaccharide selected from the group consisting of maltitol, maltitritol, maltitetraol, lactitol and mixtures thereof.

5. The semi-paste oral preparation of claim 1, further comprising a wetting agent, thickener, foaming agent, stabilizer, sweetening agent, antiseptic, perfume, coloring agent, or combinations thereof.

6. The semi-paste oral preparation of claim 5, wherein said wetting agent is selected from the group consisting of glycerin, sorbitol, propylene glycol, polyethylene glycol or mixtures thereof.

7. The semi-paste oral preparation of claim 5, wherein said thickener is selected from the group consisting of sodium carboxymethyl cellulose, hydroxyethyl cellulose, carrageenan, sodium alginate, xanthane gum, polysodium acrylate, polyvinyl alcohol, locust bean gum, Carbopol, guar gum, montmorillonite, gelatin, carboxyvinyl polymer, hydroxypropyl methyl cellulose, and mixtures thereof.

8. The semi-paste oral preparation of claim 5, wherein said foaming agent is selected from the group consisting of sodium laurylsulfate, sodium $\alpha$-olefinsulfates, N-acylgarcosinates, N-acylglutamates, N-acyltaurates, sucrose fatty acid esters, armalolamnide, polyoxyethylene hydrogenated castor oil, and polyglycerin fatty acid esters, and combinations thereof.

9. The semi-paste oral preparation of claim 5, wherein said sweetening agent is selected from the group consisting of saccharin sodium, itevioside, p-methoxycinnamin aldehyde, neohesperidyl dihydrochalaoone, perillartine, and mixtures thereof.

10. The semi-paste oral preparation of claim 5, wherein said antiseptic is selected from the group consisting of p-oxyhydroxybenzoic esters, sodium benzoate, and mixtures thereof.

11. The semi-paste oral preparation of claim 1, further comprising an effective amount of a pharmaceutically acceptable fluoride ion.

12. The semi-paste of claim 1, which provides at least about 86% remaining effective povidone-iodine after exposure to storage conditions of 40° C. for 3 months.

* * * * *